(12) United States Patent
Huelskamp

(10) Patent No.: US 7,085,952 B2
(45) Date of Patent: Aug. 1, 2006

(54) METHOD AND APPARATUS FOR WRITING DATA BETWEEN FAST AND SLOW CLOCK DOMAINS

(75) Inventor: Paul J. Huelskamp, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 483 days.

(21) Appl. No.: 10/167,749

(22) Filed: Jun. 10, 2002

(65) Prior Publication Data
US 2003/0056137 A1   Mar. 20, 2003

Related U.S. Application Data

(63) Continuation-in-part of application No. 09/952,914, filed on Sep. 14, 2001.

(51) Int. Cl.
*G06F 1/12* (2006.01)
*G06F 1/32* (2006.01)
*A61N 1/00* (2006.01)

(52) U.S. Cl. .................... 713/600; 713/320; 607/2

(58) Field of Classification Search ............... 713/600, 713/400, 375, 322, 320; 607/16, 60, 2; 711/103
See application file for complete search history.

(56) References Cited

U.S. PATENT DOCUMENTS

| | | | |
|---|---|---|---|
| 4,592,360 A * | 6/1986 | Lesnick | 607/60 |
| 5,022,395 A | 6/1991 | Russie | |
| 5,254,888 A * | 10/1993 | Lee et al. | 327/298 |
| 5,533,032 A | 7/1996 | Johnson | |
| 5,633,742 A * | 5/1997 | Shipley | 398/118 |
| 6,601,131 B1 * | 7/2003 | Sezaki et al. | 711/103 |
| 6,819,150 B1 * | 11/2004 | Santosa et al. | 327/141 |

FOREIGN PATENT DOCUMENTS

| | | | |
|---|---|---|---|
| EP | 406830 A2 * | 1/1991 | |
| EP | 468680 A2 * | 1/1992 | |

OTHER PUBLICATIONS

Stotts, Introduction to Implantable Biomedical IC Design, 1989, IEEE, pp. 12-18.*

* cited by examiner

*Primary Examiner*—Thomas Lee
*Assistant Examiner*—Suresh K Suryawanshi
(74) *Attorney, Agent, or Firm*—Michael C. Soldner; Girma Wolde-Michael

(57) ABSTRACT

A system for writing data efficiently between a fast clock domain and a slow clock domain. In one embodiment, a processor that performs firmware routines is clocked by a fast clock that is turned on when a prescribed event occurs to operate in the fast clock domain in conjunction with hardware that performs certain device operations that is clocked by a slow clock that is always on to operate in a slow clock domain. Writing data from the processor to the hardware involves determining if a bit is to be written to a register of the slow clock domain in synchrony with a transition of the slow clock, stopping the fast clock to pause operation of the processor, writing the bit to the register of the slow clock domain upon a succeeding slow clock transition, and starting the fast clock to resume operation of the processor.

2 Claims, 17 Drawing Sheets

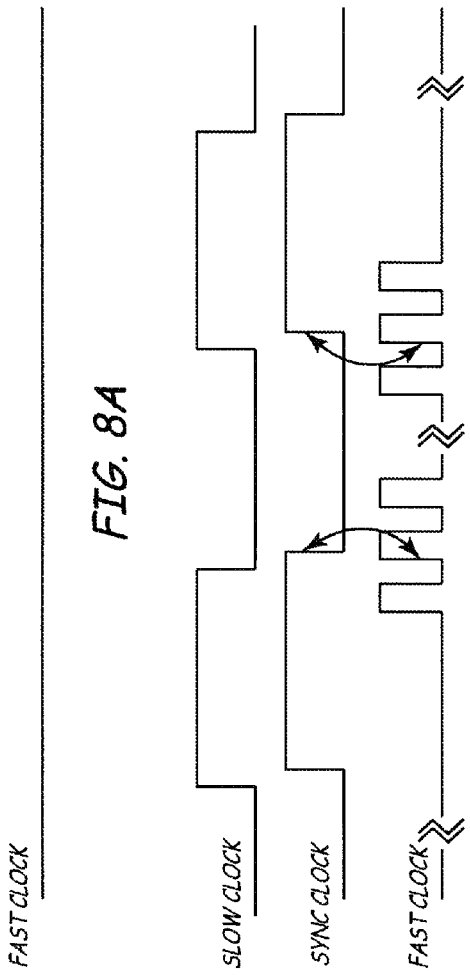

METHOD AND APPARATUS FOR WRITING DATA BETWEEN FAST AND SLOW CLOCK DOMAINS

REFERENCE TO RELATED APPLICATION

This application is a continuation-in-part of U.S. patent application Ser. No. 09/952,914 filed Sep. 14, 2001 in the names of Splett et al. and entitled METHOD AND APPARATUS FOR SYNCHRONIZATION OF CLOCK DOMAINS.

FIELD OF THE INVENTION

This invention relates generally to implantable medical devices of the type comprising electronic circuitry performing monitoring of a physiologic state and/or therapy delivery employing a fast clock and a slow clock and particularly to writing data between fast and slow clock domains under certain conditions.

DESCRIPTION OF THE RELATED ART

The technology explosion in the implantable medical device (IMD) industry has resulted in many new and innovative devices and methods for analyzing the health of a patient and/or providing therapies to improve quality of life. IMDs include pacemakers, implantable cardioverter-defibrillators (ICDs), neural stimulators, drug administering devices, monitors, etc. State-of-the-art IMDs are capable of performing significantly more complex tasks and are vastly more sophisticated and complex than earlier IMDs and their therapeutic benefits have been well established.

There are many IMDs that provide data acquisition of important physiologic data from a human body, e.g. cardiac IMDs that acquire cardiac data. Such cardiac IMDs include implantable heart monitors that only monitor and acquire cardiac data and therapy delivery IMDs that both acquire cardiac data and provide appropriate therapies, such as single chamber, dual chamber, and bi-ventricular pacemakers, ICDs that typically incorporate pacing systems for treating bradycardia and tachyarrhythmias, and cardiomyostimulators. The therapy delivery cardiac IMDs comprise an implantable pulse generator (IPG) that is coupled with one or more electrical medical lead bearing electrodes for sensing the inter-cardiac or remote electrogram (EGM) and/or delivering pacing pulses or cardioversion/defibrillation shocks to the heart.

Cardiac IMDs and other IMDs can include the capability of communicating, through radio frequency telemetry transmissions, with external medical devices to enable programming and interrogation of the IMD through downlink telemetry transmissions and to enable uplink telemetry transmissions of data from the IMD to the external medical device.

Cardiac IPGs and monitors as well as other IMDs are powered by an internal power source, typically one or more battery, that serve a variety of functions, including, but not limited to, supplying power to electronic components and circuitry and charging high voltage capacitors that are discharged through medical electrical leads into the heart to regulate heart rhythms. The functional sophistication and complexity of the IMD operating systems powered by the battery have increased over the years. Battery powered IMDs must be replaced when the battery(s) become depleted, and therefore conserving battery power is important to maintain or prolong the life of the IMD. Therefore, much effort has been devoted to increase conservation of battery resources.

Typically, the IPG or monitor operating system comprises a microcomputer (referred to herein as a processor or CPU) operating in accordance with stored software (referred to herein as "firmware") that is clocked by a fast clock and other CMOS ICs and discrete components (referred to as "hardware") that are either clocked by a slow clock or by the fast clock. Thus, certain circuitry operates in a "fast clock domain or mode" and other circuitry operates in a "slow clock domain or mode". The operating modes can be characterized by one or more finite state machine that involves the hardware and/or software. Generally speaking, power is conserved by clocking hardware of the slow clock domain by the slow clock and only operating the fast clock when it is necessary to run the processor and/or certain hardware in the fast clock domain.

Use of multi-mode operation may lead to more efficient use of battery power; however, switching between the slow and fast clock mode operations may cause switching errors, e.g., ringing, false signal rises, etc. Such errors can cause malfunction of a circuit, making the overall implantable medical system unpredictable at times. Errors occurring in IMDs can cause harm to the health of a patient.

The present invention is directed to overcoming, or at least reducing the effects of, one or more of the problems set forth above.

SUMMARY OF THE INVENTION

The present invention is preferably embodied in an IMD of the type performing monitoring of a physiologic state and/or therapy delivery under the control of a system comprising a processor that performs firmware routines and is clocked by a fast clock that is turned on when a prescribed event occurs to operate in a fast clock domain and hardware that performs certain device operations and is clocked by a slow clock that is always on to operate in a slow clock domain. The hardware operations can be characterized by states and transitions between states of a finite state machine.

Generally, the present invention provides an improved method and system for writing data from the processor to the hardware that involves determining if a bit is to be written to a register of the slow clock domain in synchrony with a transition of the slow clock, stopping the fast clock to pause operation of the processor, and writing the status bit to the register of the slow clock domain and starting the fast clock to resume operation of the processor upon a succeeding slow clock transition.

Preferably, the slow clock is provided to the slow clock domain at all times, and the fast clock is turned on when an operation of the processor is required. The operation of the processor can include writing to or reading data from the slow clock domain. A slow sync clock is generated when the fast clock is turned on to synchronize the clock transitions of the slow sync clock to a clock transition of the fast clock. The slow sync clock is substituted for the slow clock provided to the slow clock domain for the duration of the fast clock.

The present invention advantageously reduces the need to cycle the fast clock and consume energy while awaiting the slow clock.

BRIEF DESCRIPTION OF THE DRAWINGS

The invention may be understood by reference to the following description taken in conjunction with the accompanying drawings, in which like reference numerals identify like elements, and in which:

FIGS. 8a and 8b illustrate a timing diagram relating to synchronization of clock domains, in accordance with one exemplary embodiment of the present invention;

Figure 1:
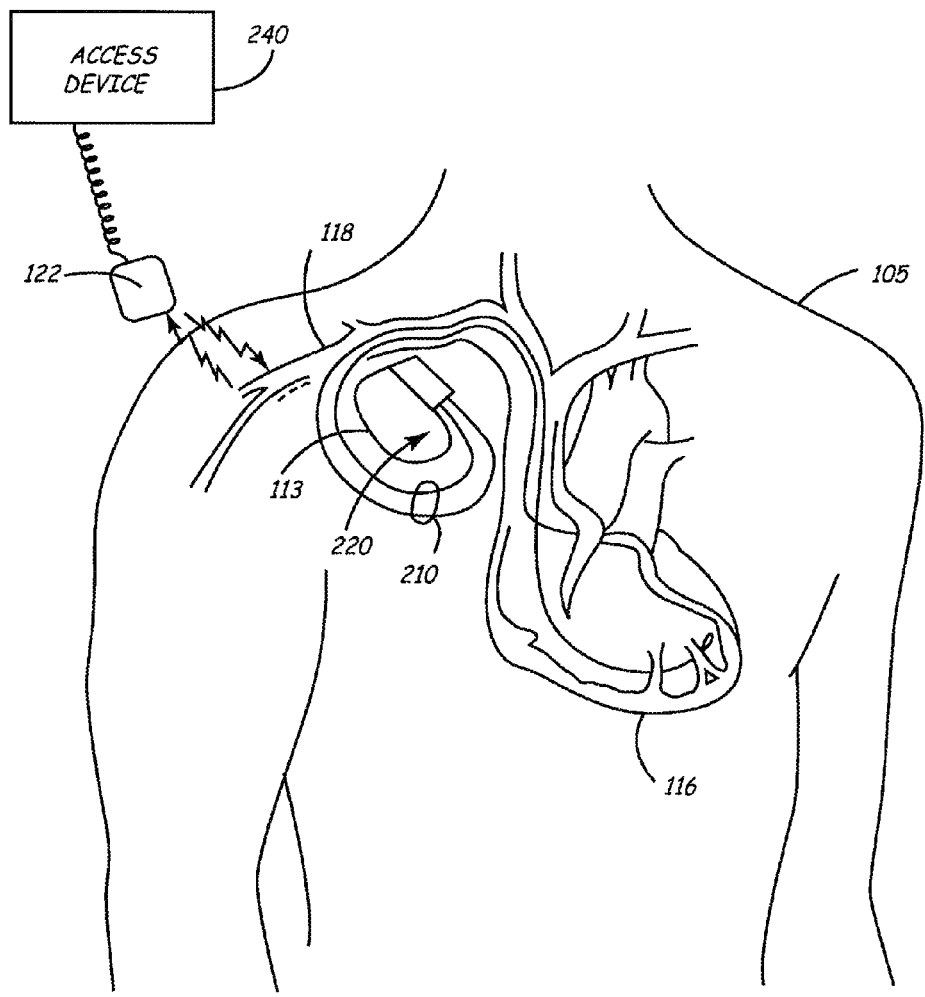
FIG. 1 is a simplified diagram of an implementation of an IMD in accordance with one exemplary embodiment of the present invention.

Appendix A provides an example of implementing a hardware descriptive language to provide the synchronization of clock domains, in accordance with one embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF PREFERRED EMBODIMENTS

Exemplary embodiments of the invention are described below particularly with respect to FIGS. 14a, 14b and 15. The present invention can be practiced in the context of the systems of FIGS. 1–13b. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

There are many discrete processes involving collecting, storing, and presenting physiologic trends of a patient, as well as in delivering therapies (e.g., a cardiac therapy). The battery located within an IMD provides the power necessary for performing such operations. Therefore, conserving battery power can provide for longer, uninterrupted operation of the IMD. Many systems utilize a sleep mode when a certain portion of a circuit in the IMD is not immediately needed, in order to conserve power. Often, a different clock rate may be used for a sleep mode operation, whereas a faster clock rate may be used for normal operation that requires more robust circuit functions. For example, simple monitoring functions may be performed using a slower operation clock frequency while more complex circuitry in the IMD may be used in a sleep mode. A fast clock is invoked upon detection of a cardiac event in order to process acquired physiologic data and deliver a cardiac therapy in response to the processing of the physiologic data. Certain errors, ringing, false signal rises (glitches), etc., may occur when switching from one clock to another (e.g., switching from a slow clock to a fast clock or from a fast to slow clock) that can cause malfunction of a circuit making the IMD operation unreliable.

FIG. 1 illustrates one embodiment of a cardiac IMD 220, particularly a pacemaker or implantable cardioverter-defibrillator IPG 113 incorporating a pacing system and attached leads 210, implanted in a human body 105. The present invention can be incorporated into such a cardiac IMD 220 or into other IMDs of the types described above and is merely described for convenience in reference to a pacing IPG 113.

The circuitry, battery and other components of the IPG 113 are contained within a hermetically sealed, biologically inert outer canister or housing that may be conductive so as to serve as a pace/sense electrode in the pacing/sensing circuit. One or more lead collectively identified with reference numeral 210 in FIG. 1 are electrically coupled to the IPG 113 and extend into the patient's heart 116 via a vein 118. One or more exposed conductive pace/sense electrode(s) for sensing electrical cardiac signals or delivering electrical pacing pulses to the heart 116 are disposed at or near the distal ends of the leads 210. The leads 210 may be implanted with their distal ends situated in the atrium and/or ventricles of the heart 116 or elsewhere in cardiac blood vessels in operative relation with a heart chamber as is well known in the art. The leads 210 can also carry other sensors or sensing cardiac physiologic data, e.g. pressure, temperature, impedance, pH, blood gas, acceleration, etc.

The IPG 113 collects and processes a plurality of data acquired from the human body through the sensors of the leads 210. The data acquired by the IPG 113 can be uplink telemetry transmitted to an access device 240, e.g., a programmer comprising a programming head 122 that remotely communicates with the IPG 113. The programming head 122 is utilized in accordance with medical device programming systems known those skilled in the art having the benefit of the present disclosure, for facilitating two-way uplink and downlink telemetry communications between the IPG 113 and the access device 240.

Figure 2:
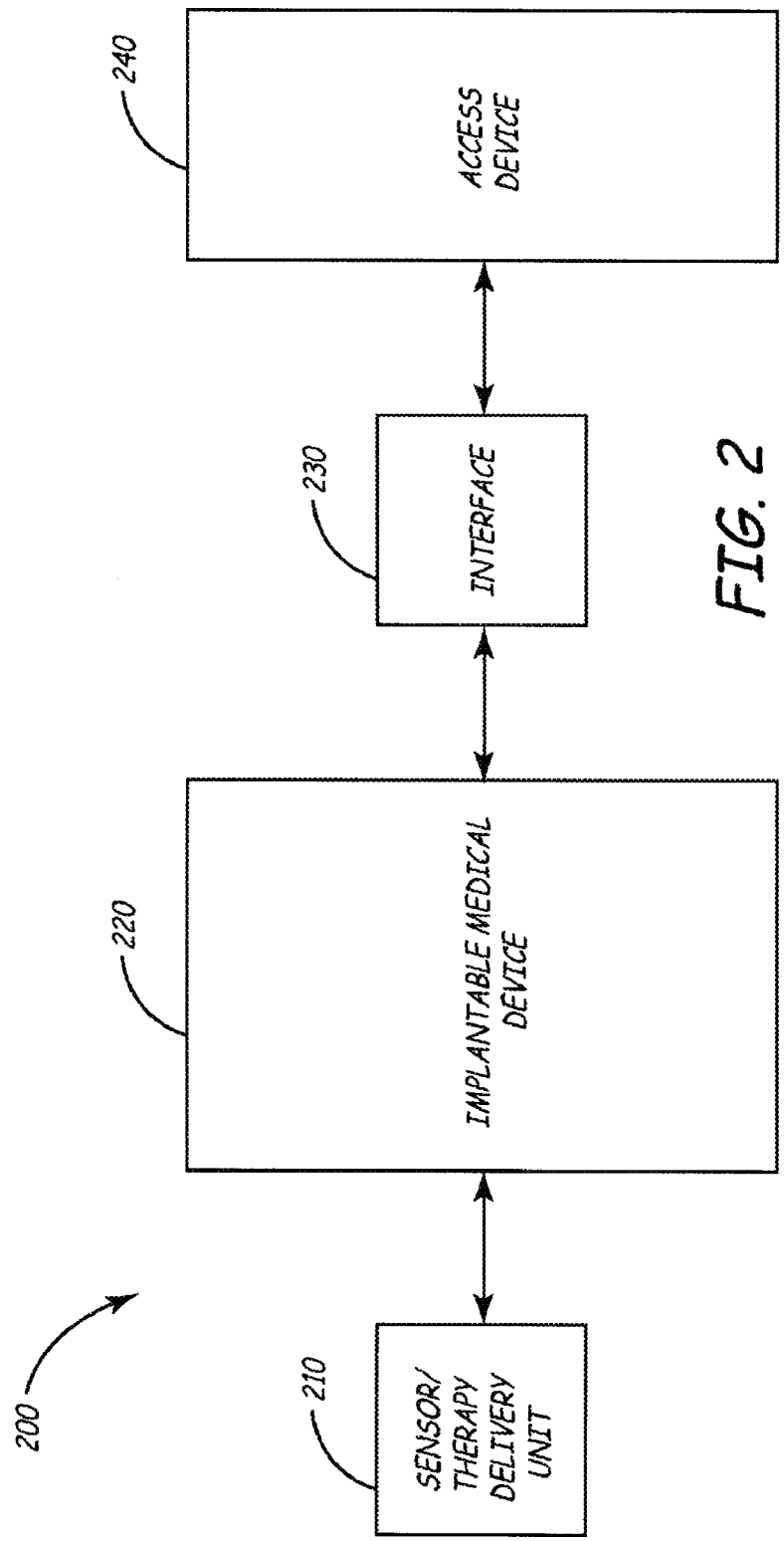
FIG. 2 illustrates a simplified block diagram representation of an IMD system in accordance with one exemplary embodiment of the present invention.

The leads 210, the IPG 113, the access device 240, and a system interface 230 between the cardiac IMD 220 and the access device 240 can be characterized as the system 200 illustrated in FIG. 2. The system interface 230 provides a communication link between the cardiac IMD 220 and the access device 240. The operating system of the IPG 113 acquires and stores physiologic data in memory as described above. The access device 240 can be used at a later time to interrogate the memory of the IPG 113 to receive the uplink telemetry transmitted data via the interface 230.

Generally, the interface 230 is a telemetry interface that is capable of facilitating two-way communications between the access device 240 and the cardiac IMD 220. In one embodiment, the interface 230 includes circuitry and components of and provides wireless telemetry between the access device 240 and the cardiac IMD 220. Any of the hardware implementations and processes that are known by those skilled in the art having benefit of the present disclosure can be used in telemetry interface 230 for telemetry communications.

Figure 3:
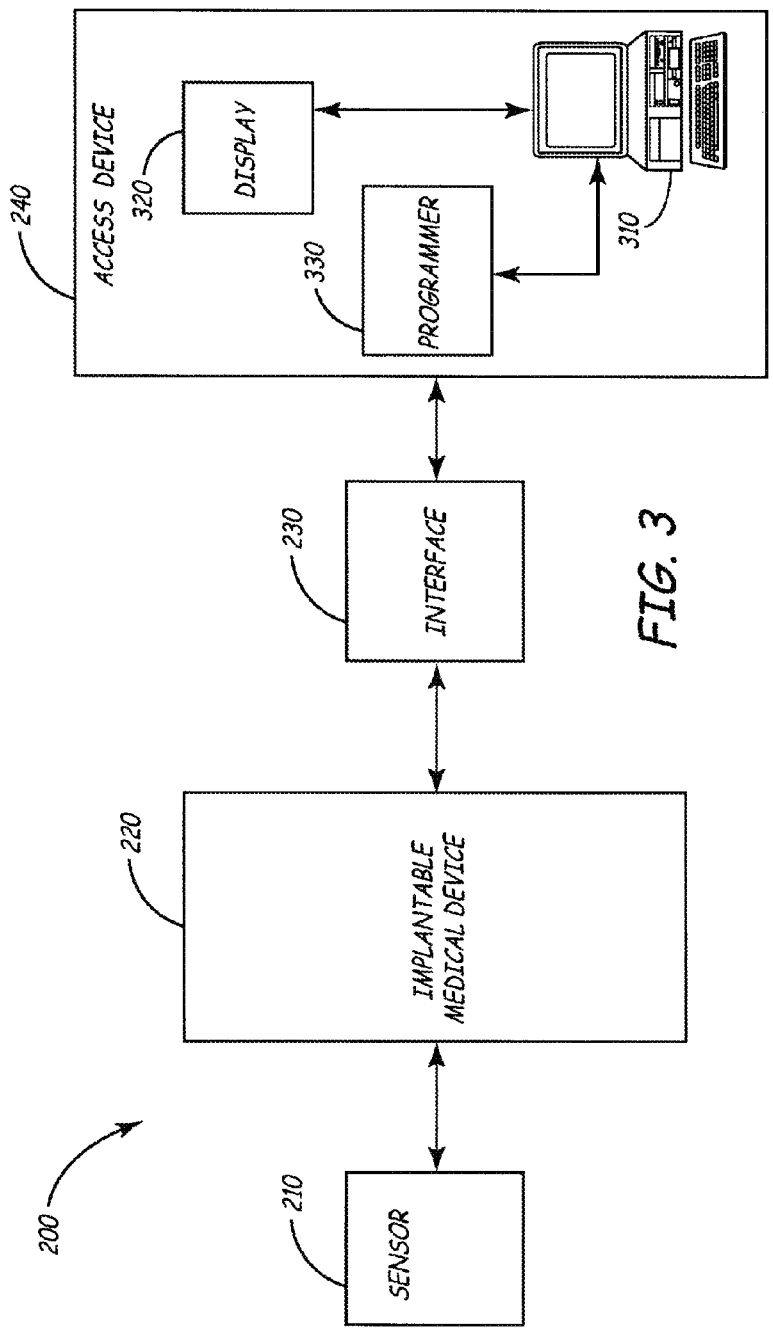
FIG. 3 illustrates a more detailed block diagram representation of an access device of FIG. 2, in accordance with one exemplary embodiment of the present invention.

FIG. 3 illustrates a more detailed illustration of the access device 240. In one embodiment, the access device 240 comprises a computer system 310, a display device 320, and a programmer 330. In one embodiment, the programmer 330 can be integrated into the computer system 310. The computer system 310 can prompt the acquisition of physiologic data from the cardiac IMD 220 via the interface 230. The computer system 310 can then display the physiologic data on the display device 320. The display device 320 can display physiologic data from the reference point of different time periods, different activity results, and the like.

Figure 4:
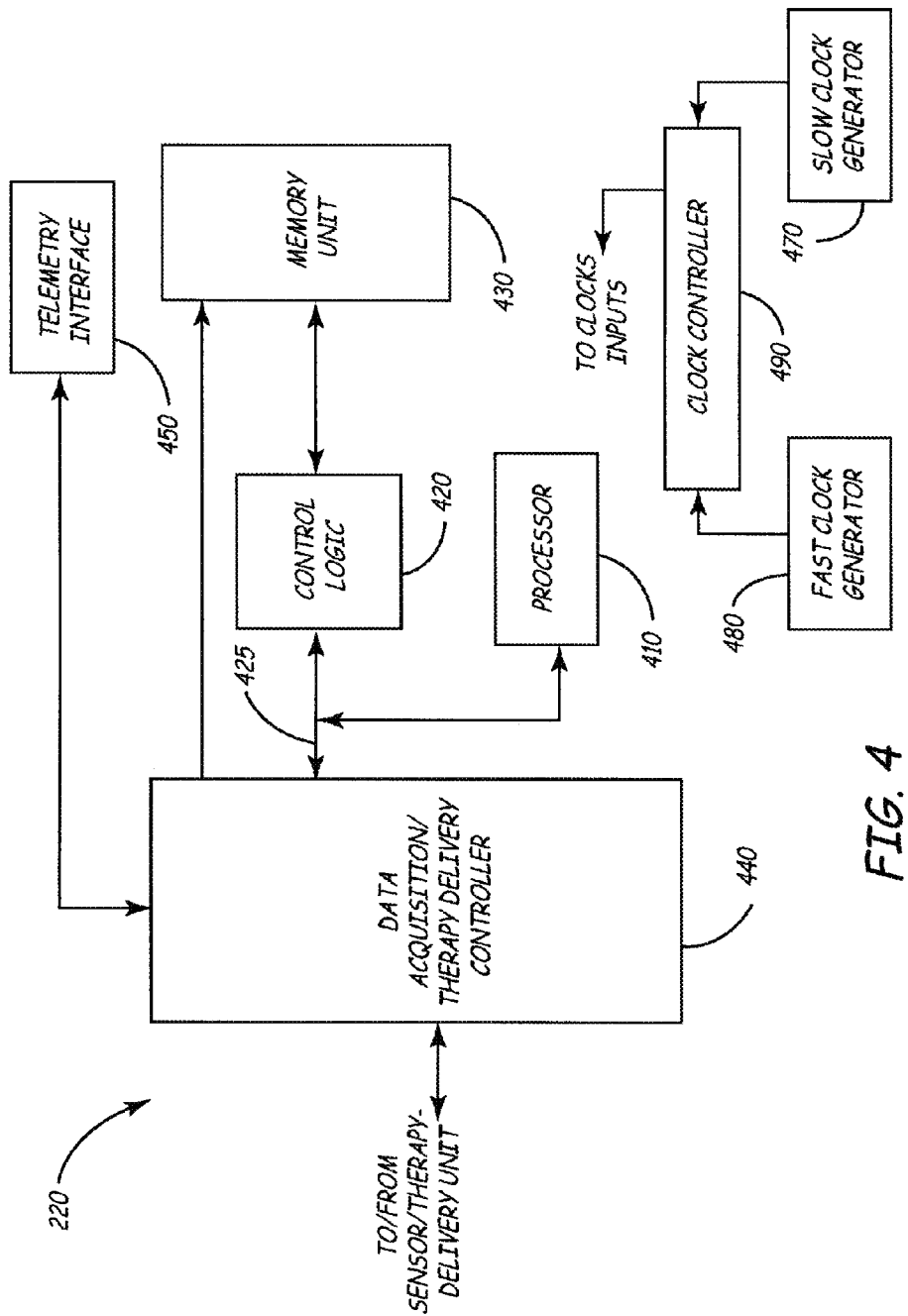
FIG. 4 illustrates a more detailed block diagram representation of an IMD of FIG. 2, in accordance with one exemplary embodiment of the present invention.

Turning now to FIG. 4, a more detailed block diagram depiction of one embodiment of the cardiac IMD 220 is illustrated. The cardiac IMD 220 comprises a processor 410, control logic 420, a memory unit 430, a data acquisition controller 440, a telemetry interface 450, a slow clock generator 470, a fast clock generator 480, and a clock controller 490.

For example, the slow clock generator 470 produces a raw 32 KHz clock denoted osc_32 KHz that is supplied to the clock controller 490. The clock controller develops a plurality of 32 KHz clocks from the raw 32 KHz clock including a slow clock denoted 32 KHz_slow in FIG. 12 and at least one slow sync clock as described further herein. The fast clock generator 480 generates a clock of a frequency of approximately 2.8 MHz denoted osc_hf(2.8 MHz) in FIG. 12. The 2.8 MHz clock is divided down by 4 to provide a plurality of 700 MHz clocks shown in FIG. 12 including a 700 MHz cpu_clock shown in FIG. 12 that clocks the processor 410.

The control logic 420 sends control signals to the memory unit 430 for controlling memory 430, and to the data acquisition controller 440, which controls the acquisition of physiologic data and drives output signals to the telemetry interface 450. The telemetry interface 450 can facilitate real-time access of physiologic data acquired by the data acquisition controller 440. A physician can employ the telemetry interface 450 to operate the data acquisition controller in real time to gather and view physiologic data uplink telemetry transmitted to the access device 240.

In one embodiment, the control logic 420, the data acquisition controller 440, the telemetry interface 450, and the clock controller 490 are implemented in digital circuitry or digital signal processors or the like referred to herein as "hardware" and operate following defined state and state transitions of one or more finite state machine.

The control logic 420, the data acquisition controller 440, and the clock controller 490 are normally clocked by the slow clock generator 470 to operate in a slow clock mode and can individually or collectively be characterized as constituting a "slow clock domain". Among other things, the slow clock is employed in the slow clock domain to time out intervals, e.g., diagnostic intervals, pacing escape intervals and other intervals timed out by timers, associated with delivery of pacing pulses and detection of sense events in accordance with a programmed pacing mode and pacing parameters and/or cardioversion/defibrillation functions and the like, depending upon the particular IMD. The slow clock generator 470 provides the operational clock for the cardiac IMD 220 during normal operating modes as described herein.

The processor 410 comprises a CPU of a micro-computer and is sometimes referred to as a CPU herein. The processor 410 and the memory unit 430 are clocked by the 700 MHz fast clock (cpu_clock in FIG. 12) generated by the clock controller 490 from the 2.8 MHz clock output by the fast clock generator 480. The 700 MHz fast clock (cpu_clock in FIG. 12) also clocks the telemetry interface 450 during telemetry and high voltage capacitor charging circuitry during charge-up (in the cardioversion/defibrillation context). The clock controller 490 invokes the fast clock generator 480 when certain events occur that are described further below. The processor 410 functions at the fast clock speed under the control of software algorithms stored in memory unit 430 (referred to herein as "firmware") and in response to interrupts and handshake signals from the hardware to run its operations and to trigger operations of one or more of the slow clock domain components of the cardiac IMD 220. For example, the processor 410 operates control logic 420 to perform a plurality of operations, including memory access and storage operations, physiologic data processing, and therapy delivery operations. The processor 410 communicates with the memory unit 430 and the slow clock domain components via an address and data bus 425 that can be implemented in an 8-bit or 16-bit parallel bus architecture. Data bits are transmitted over the address and data bus 425 from the fast clock domain to registers of the slow clock domain at the fast clock frequency and from the slow clock domain to the fast clock domain at the slow clock frequency.

In one embodiment, the firmware invokes the slow clock generator 470 to enter a slow clock mode (slow clock domain) that utilizes less power than the fast clock. The fast clock mode is invoked when a physiologic event (e.g., a cardiac sense event) is detected. Furthermore, the fast clock mode may be invoked at predetermined intervals (e.g., once every 1000 milliseconds) to perform diagnostics operations, such as memory refreshing, lead diagnostics, battery measurements, and the like. In one embodiment, the transition from a slow clock domain to a fast clock domain comprises changing the circuit operation from a slow clock operating frequency to a fast clock operating frequency during a non-transition period of the slow clock. Furthermore, when the fast clock mode is invoked, the slow clock is synchronized to the fast clock and a slow sync clock is developed. The slow sync clock is employed by the hardware components of the slow clock domain as long as the fast clock mode is invoked. Without the slow sync clock, simply turning on the fast clock and continuing to clock the hardware components of the slow clock domain at the slow clock can cause jitters, unintended rising edges in certain digital signals, etc. as described above. The use of the fast clock may be delayed until the slow clock is synchronized with the fast clock. As a result, the initial operation performed by the cardiac IMD 220 in the fast clock mode would be synchronized with the operation of the cardiac IMD 220 in the slow clock mode. The overall stability of the circuitry in the cardiac IMD 220 is improved by synchronizing the fast and slow clocks.

Figure 5:
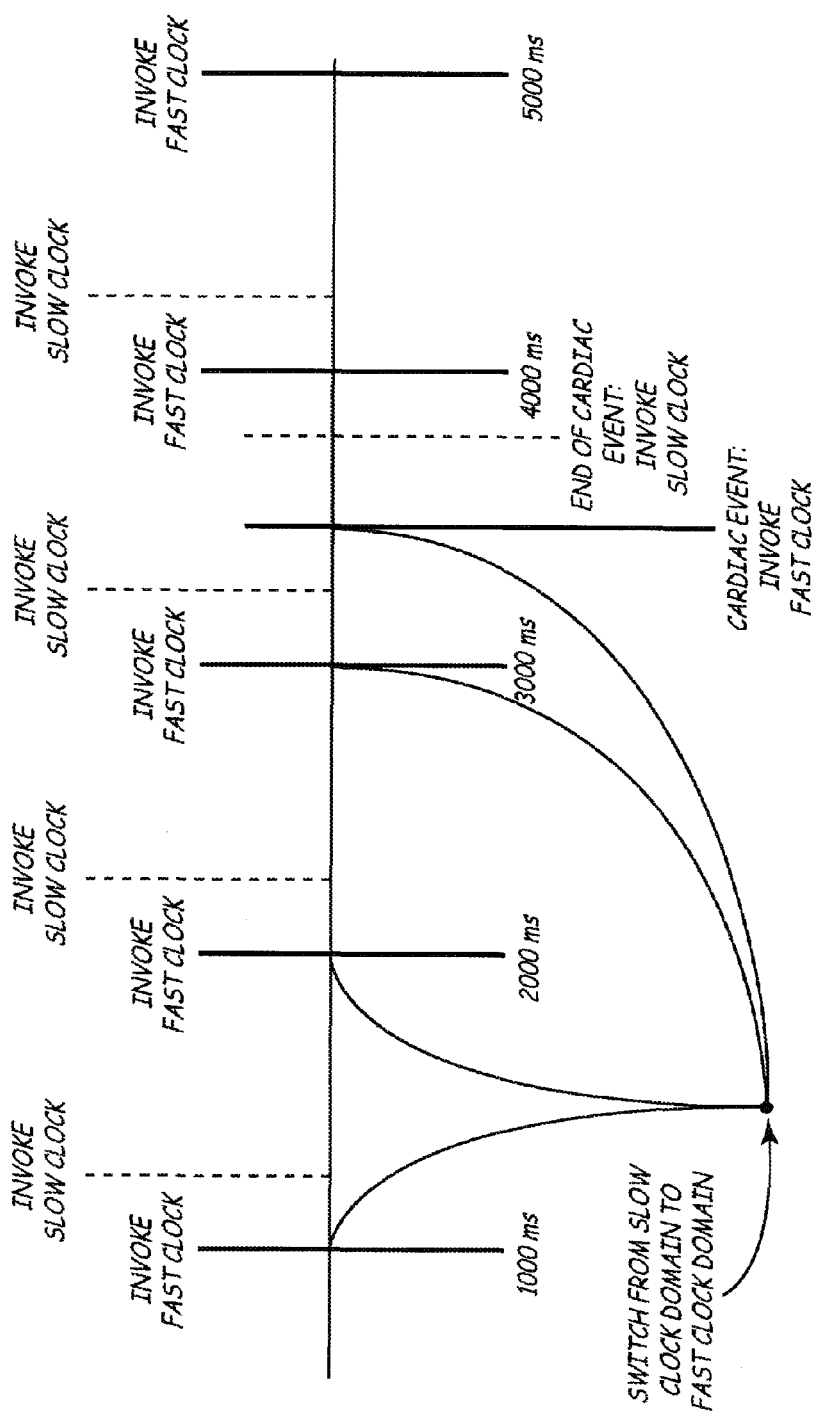
FIG. 5 illustrates a time-line diagram of a clock switching function in accordance with one embodiment of the present invention.

FIG. 5 depicts a timing diagram illustrating a sample of events that show the slow clock and the fast clock transitions in accordance with one embodiment of the present invention. As indicated in FIG. 5, the fast clock generator 480 is invoked at approximately one-second diagnostic intervals (1,000 millisecond intervals) to allow the processor 410 to rapidly perform certain circuit diagnostic functions. These diagnostic functions include performing a memory refresh task, logging of certain status signals into memory, checking impedance and other electrical characteristics of the lead 210, measuring battery state, and the like. The fast clock is stopped after the certain diagnostic routines are completed. The slow clock generated by the slow clock generator 470 clocks the operation of certain of the hardware components of the slow clock domain of the cardiac IMD 220.

Thus, in the example of FIG. 5, the slow clock domain circuitry of the cardiac IMD 220 is clocked at the slow clock frequency until each depicted 1,000 millisecond diagnostic interval is timed out and the fast clock is invoked. The fast clock is invoked at the 2,000 millisecond mark, the 3,000 millisecond mark, and so on as shown in FIG. 5.

The fast clock is also invoked when certain events transpire during time-out of the diagnostic intervals that function as interrupts to the processor 410, e.g., a cardiac event, achievement of a device state, a wake-up request, or a telemetry request and other interrupt requests. Cardiac events can include sense events of particular features of the cardiac electrogram that satisfy detection criteria of sense amplifiers incorporated into the data acquisition controller 440. Cardiac events include delivery of a pacing pulse in the context of a cardiac pacemaker. In the cardioversion/defibrillation context, the circuitry processes sense events to determine whether the timing of a succession of sense events satisfies malignant tachyarrhythmia criteria and, if so, starts charge-up of high voltage cardioversion/defibrillation capacitors. The state of charge is monitored and a device state interrupt is generated when the cardioversion/defibrillation capacitors are charged to programmed discharge voltage.

For example, the cardiac IMD 220 operates at a slow clock frequency after the 3,000 millisecond mark until a cardiac event is detected as illustrated in FIG. 5. The processor 410 performs a firmware routine clocked by the fast clock in response to the cardiac event and then turns the fast clock off to conserve battery energy. The processor 410 again performs diagnostic routines at the 4,000 and the 5,000 millisecond marks depicted in FIG. 5

Figure 6:
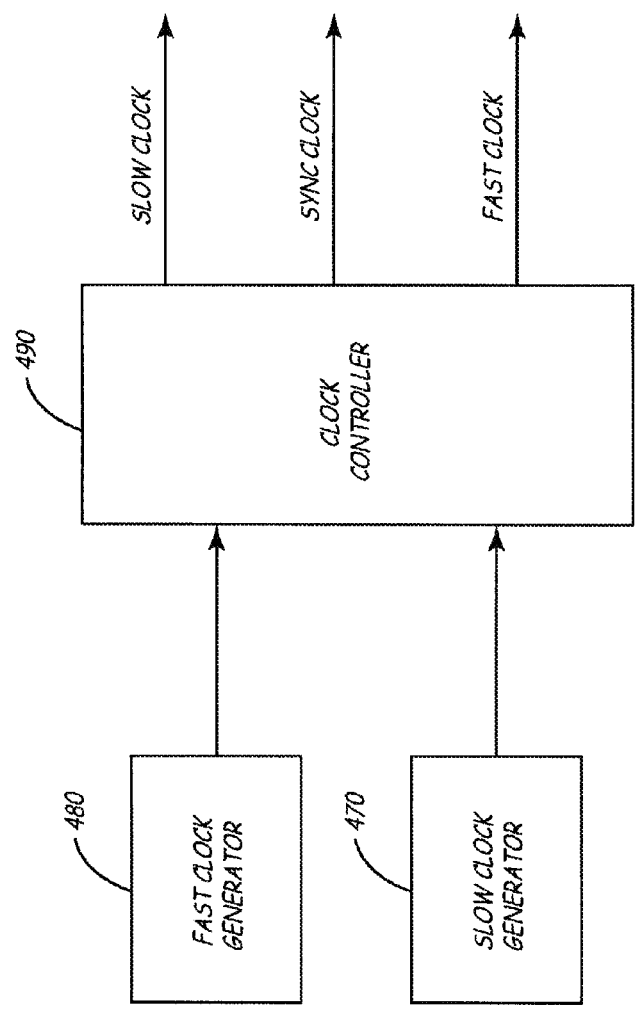
FIG. 6 illustrates a block diagram representation of the operation of a clock controller of FIG. 4, in accordance with one exemplary embodiment of the present invention.

A block diagram representation of an interaction between the fast clock generator 480, the slow clock generator 470, and the clock controller 490 is illustrated in FIG. 6. Clock frequency signals generated by the fast clock generator 480 and the slow clock generator 470 are sent to the clock controller 490. The clock controller 490 controls the switching of certain digital signals that control the clock operations of other circuitry in the cardiac IMD 220. The clock controller 490 provides a slow clock, a slow sync clock, and a fast clock. In an alternative embodiment, the slow sync clock and the slow clock are generally on one signal line.

Figure 7:
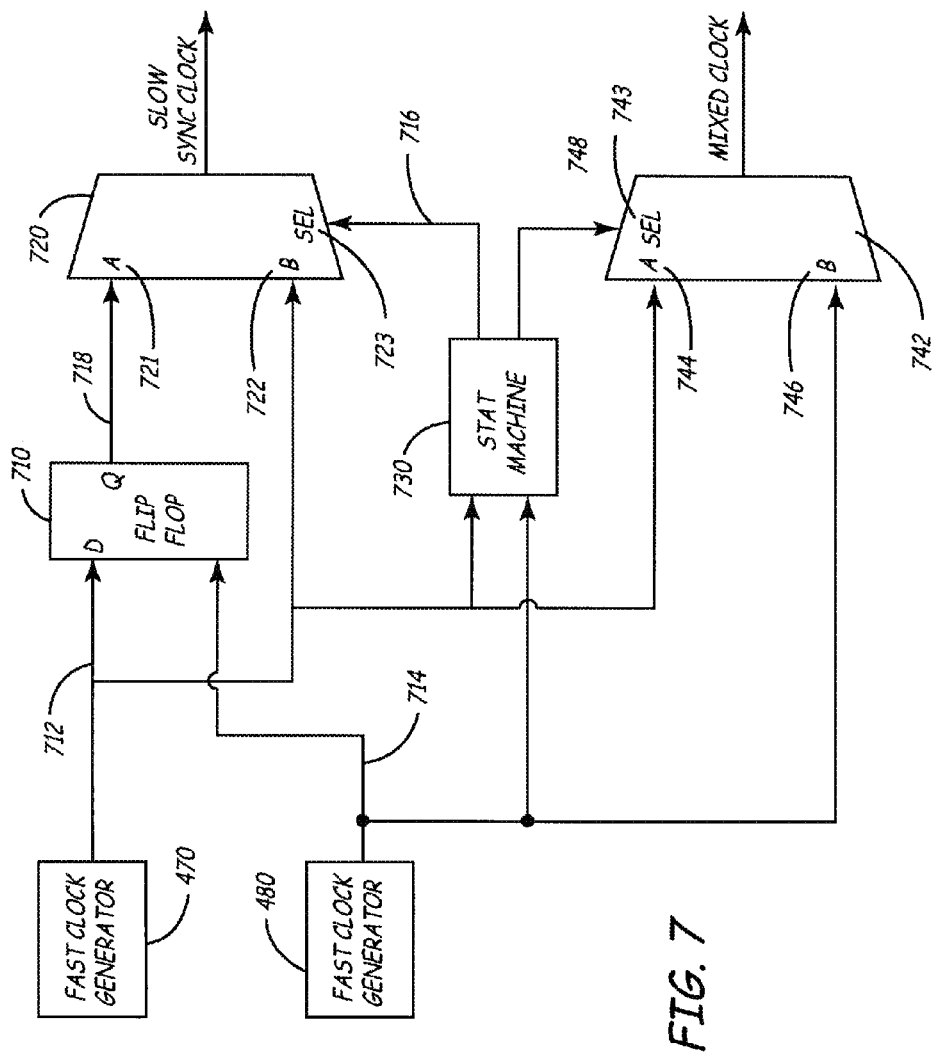
FIG. 7 illustrates a block diagram representation of the clock controller of FIG. 4, in accordance with one exemplary embodiment of the present invention.

A more detailed representation of the clock controller 490 is provided in FIG. 7. The clock controller 490 comprises a D-type flip-flop 710, a multiplexer 720, and a state machine 730 that performs a transition from the slow clock operation to the fast clock operation. The slow clock generator 470 provides the slow clock signal to the D-type flip-flop 710 on line 712. The D-type flip-flop is also clocked by a fast clock signal output by the fast clock generator 480 on a line 714. The D-type flip-flop 710 is then used to clock the slow clock signal from the line 712 onto the output of the D-flip-flop 710 on the line 718.

The output of the D-type flip-flop on the line 718 comprises a slow sync clock that is synchronized to the fast clock (e.g., the rising and falling edge of the slow clock being synchronized to the rising edge of the fast clock), therefore reducing any jitters or other errors on a rising or falling edge transition. The slow sync clock is applied to the A input 721 of a multiplexer 720. The slow clock signal is applied to the B input 722 of the multiplexer 720 directly from the slow clock generator 470. A select signal on the line 716 from the state machine 730 is applied to select input 723 of the multiplexer 720 for selection between the slow clock and the slow sync clock. Switching from the slow clock to the slow sync clock is timed by the state machine 730 to coincide with invoking the processor 410 in the cardiac IMD 220.

FIG. 8A shows the operation of the cardiac IMD 220 during a normal power-saving mode, e.g., a sleep mode. The slow clock is on and used during the normal power saving mode operation of the cardiac IMD 220, and the fast clock is therefore not on and at base level. The state machine of the cardiac IMD 220 invokes the fast clock during certain time frames described above in reference to FIG. 5 or upon detecting certain events so that the processor 410 and other circuitry of the fast clock domain are clocked and the slow clock is synced to the fast clock. As indicated in FIG. 8B, the timing of the slow sync clock is slightly different from the timing of the slow clock. However, the fast clock (e.g., the rising edge of the fast clock) is in sync with the rising and falling edge of the slow clock. Therefore, the probability of glitches and other errors during the invocation of the fast clock is reduced.

Figure 9:
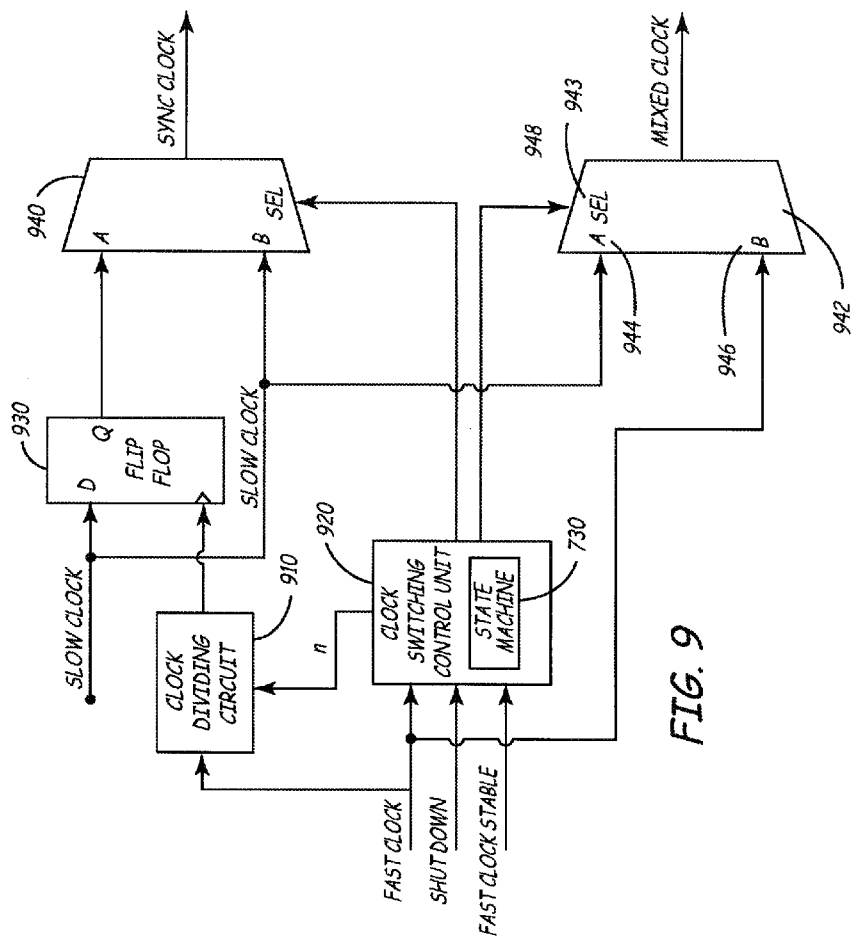
FIG. 9 illustrates a block diagram representation of performing a clock-mode switching, in accordance with one exemplary embodiment of the present invention.

The cardiac IMD 220 may comprise components that operate at a plurality of frequencies that are multiples, or fractions, of the fast clock. FIG. 9 illustrates a circuit for providing a slow sync clock at the output of multiplexer 940 that is a fraction of the frequency of the fast clock. The fast clock is divided by a value "n" in a clock dividing circuit 910. The clock switching control unit 920, which may comprise the state machine 730, provides the value "n" used to divide the clock dividing circuit 910. The slow clock is applied to one input B of the multiplexer 940, and to the D input of the flip-flop 930. The output of the clock dividing circuit 910 is used to clock the slow clock through flip-flop 930 in synchronization with the divided down fast clock and to the A input of multiplexer 940. The clock switching control unit 920 selects between the slow clock at input B and the synchronized slow clock at the input A for operation of certain components in the cardiac IMD 220. Therefore, a plurality of clock signals that are synchronized can operate a plurality of components in the cardiac IMD 220.

Figure 10:
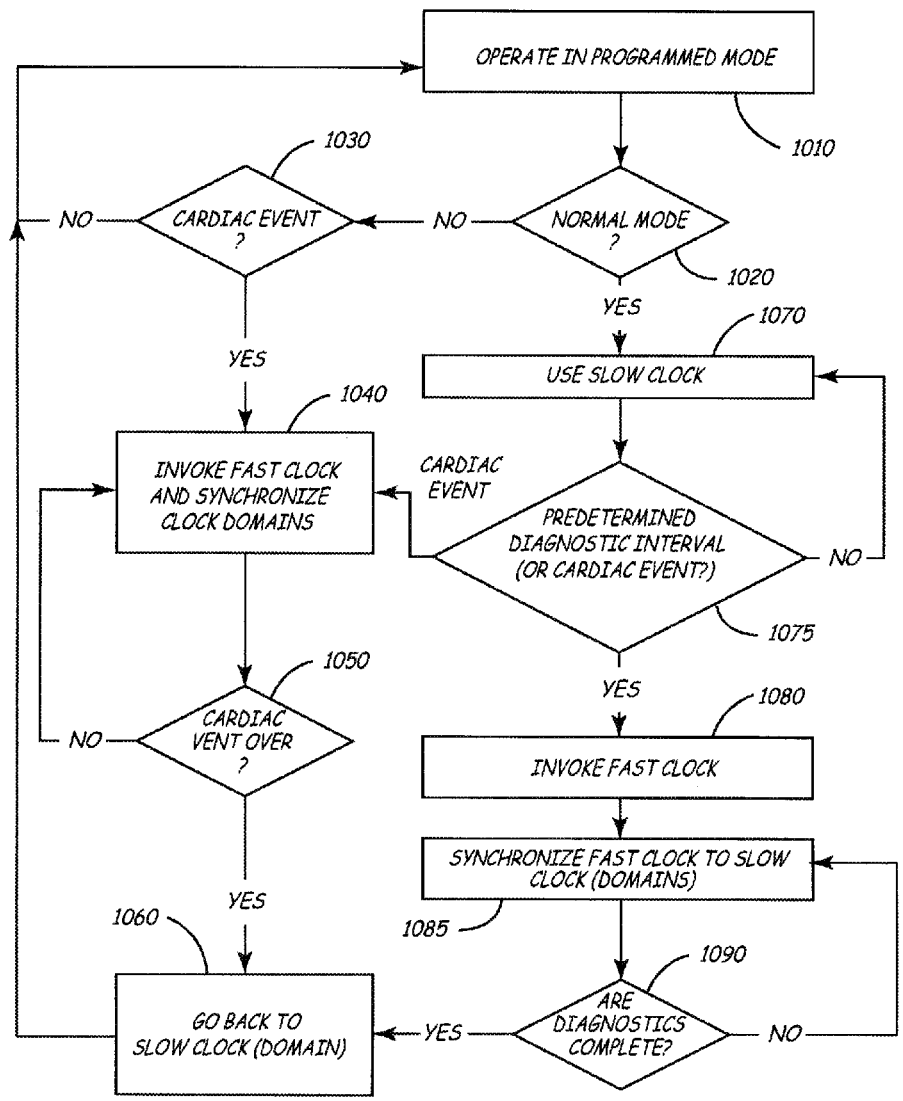
FIG. 10 is a flowchart illustrating a method in accordance with an exemplary embodiment of the present invention.

Turning now to FIG. 10, a flowchart depiction of the method in accordance with one embodiment of the present invention is illustrated. The system 200 through the interaction of the access device 240 with the cardiac IMD 220 determines an operating mode of the cardiac IMD 220 (block 1010). In other words, the mode of operation may be a normal power save mode wherein the slow clock domain components or hardware as defined above are clocked by the slow clock and the fast clock domain components, such as the processor 410, are in a low power mode and the firmware is not running. The other principal mode is the high power mode that is initiated by the operation of the fast clock wherein the fast clock domain components are operational to run the firmware. In this high power mode, either the slow sync clock of FIG. 7 or the divided down synchronized clock of FIG. 9 are generated and selected to clock the slow clock domain components or hardware while the fast clock is supplied to the fast clock domain components. As described above, the high power mode is invoked by a time-out of the predetermined diagnostic period, such as every 1,000 milliseconds, or by the detection of a certain events as described above that present interrupts to the processor 410.

The cardiac IMD 220 determines whether a normal mode is invoked in block 1020. When the cardiac IMD 220 determines that a normal mode is not invoked, the cardiac IMD 220 determines whether there is a cardiac event (block 1030). When the cardiac IMD 220 determines that there is no cardiac event, the cardiac IMD 220 again checks to determine which mode of operation is to be invoked. When the cardiac IMD 220 determines that a cardiac event, such as a cardiac sense event output by hardware or delivery of a pacing pulse by hardware has occurred (block 1030), the cardiac IMD 220 invokes the fast clock and the slow clock and fast clock domains are synchronized (block 1040). Until the cardiac event is terminated and/or all responses to the cardiac event are completed, the fast clock is invoked such that all components in the cardiac IMD 220 are operational at full capacity (see the loop from blocks 1050 to 1040 back to 1050). The cardiac IMD 220 places the operation of the cardiac IMD 220 in the slow clock mode (block 1060) when the cardiac event is determined to be over by firmware. At any given time that a cardiac event is detected, the cardiac IMD 220 is placed into a fast clock mode.

Referring to block 1020, when the implantable cardiac IMD 220 determines that a normal mode is to be maintained, the slow clock is invoked (block 1070). During the operation of the slow clock mode, the cardiac IMD 220 checks to determine whether a predetermined diagnostic interval has occurred or timed out (block 1075). Furthermore, the cardiac IMD 220 checks to determine whether a cardiac event has occurred. When the cardiac IMD 220 determines that a predetermined diagnostic time period has not occurred, the use of the slow clock is maintained. When the cardiac IMD 220 determines that a cardiac event has occurred, clock domains are changed as described above (see path from block 1075 to 1040). When the cardiac IMD 220 determines that a predetermined diagnostic time interval has been reached, the fast clock is invoked (block 1080). Subsequently, the cardiac IMD 220 syncs the fast clock to the slow clock (1085). In the low power normal mode, the diagnostic interval and other intervals, e.g., pacing escape and associated blanking and refractory intervals, are timed out in hardware timers clocked by the slow clock. The fast clock is turned on and the above-described slow sync clock is developed upon a sense event or time-out of the diagnostic interval that operate as interrupts to the processor 410. In pacing modes, non-refractory sense events trigger or inhibit pacing and may reset pacing escape intervals or start an AV delay. Time intervals between successive sense events are calculated, stored in memory and analyzed by arrhythmia detection algorithms to detect and characterize a tachyarrhythmia.

In block 1090, the cardiac IMD 220 determines whether the diagnostic process is complete as indicated by a shut down request generated by the firmware components of the cardiac IMD 220. When the diagnostic process is complete, the cardiac IMD 220 again goes back to the slow clock operation (the path from block 1090 to block 1060). The operation of the fast clock is maintained until the firmware of cardiac IMD 220 determines that the diagnostic routines are completed.

Figure 11:
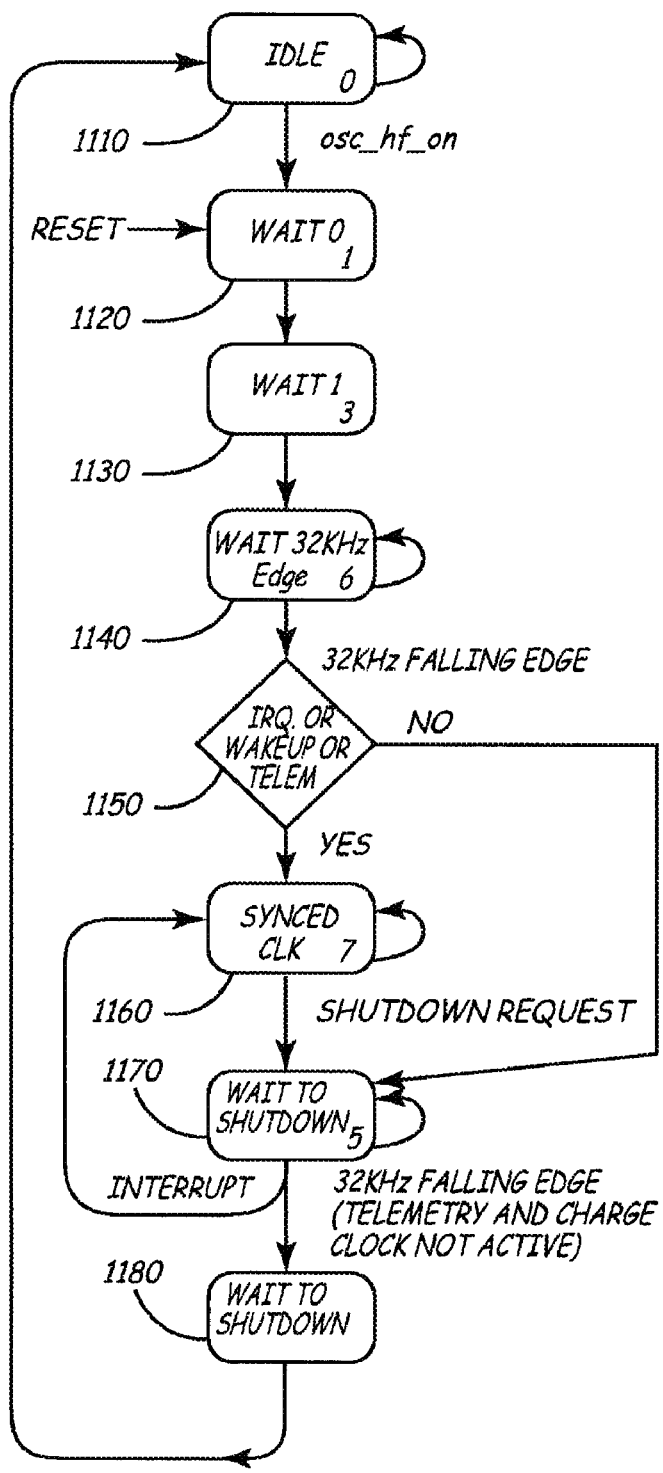
FIG. 11 illustrates a simplified depiction of a state machine in accordance with one exemplary embodiment of the present invention.
Figure 12:
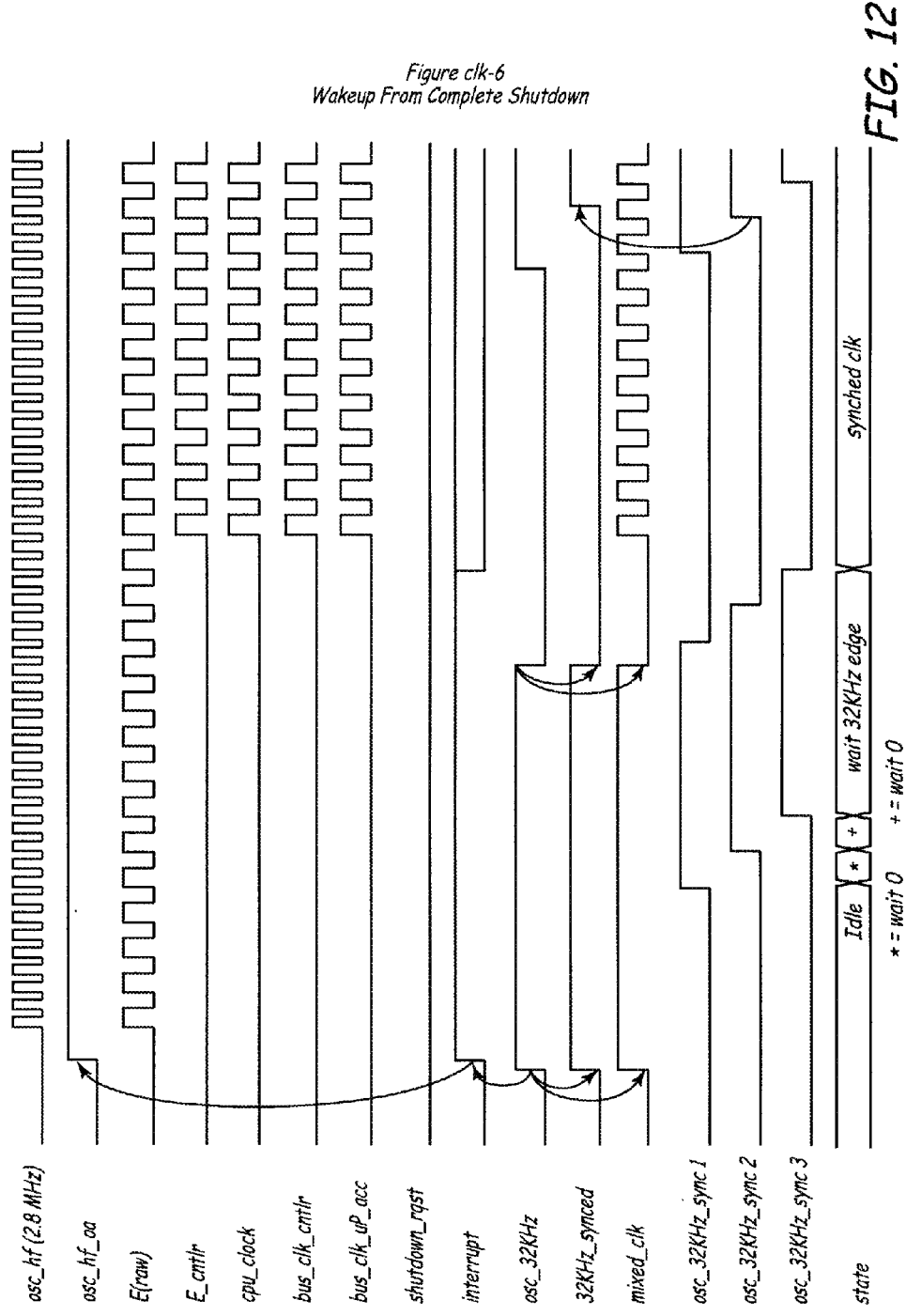
FIG. 12 illustrates a timing diagram relating to the state machine of FIG. 11, in accordance with one exemplary embodiment of the present invention.

The operations illustrated in FIG. 10 can be performed by a state machine 730 illustrated in FIG. 11 that is embodied in circuitry or "hardware" of the slow clock domain of the cardiac IMD 220 depicted in FIG. 4 and employs certain of the signals of FIG. 12. Not all of the signals of FIG. 12 are employed in the system and process of the present invention, but the signals are as follows:

osc_hf (2.8 MHz) is the raw fast clock generated by fast clock generator 480 of FIG. 4;

osc_hf_on is a hardware generated "on/off" signal of the clock controller 490 that controls the raw fast clock osc_hf signal typically by turning fast clock generator 480 on or off;

E(raw) is a 700 KHz fast clock derived from osc_hf 2.8 Mhz divided by 4 in the clock controller 490 when the raw fast clock osc_hf is turned on. The E(raw) fast clock actually clocks the processor 410 when enabled;

E_cntlr is a gated version of the E(raw) signal that is employed in the fast clock domain for purposes not relevant to the present invention;

cpu_clock is the E(raw) 700 MHz fast clock gated to the processor 410 through the clock controller 490 when the slow sync clock is developed as described above;

bus_clk_cntlr is a gated version of the E(raw) signal that is employed in the fast clock domain for purposes not relevant to the present invention;

bus_clk_uP_acc a gated version of the E(raw) signal that is employed in the fast clock domain for purposes not relevant to the present invention;

shutdown_rqst is a firmware generated request that is provided by the processor 410 to the clock controller 490 upon completion of processor operations that requests that the 2.8 MHz clock be turned off. It is absent from FIG. 12, because FIG. 12 does not show the completion of processor operations;

interrupt is any of the above described interrupts or requests generated in the hardware that requires that the processor 410 wake up and perform a function dictated by firmware and employing the cpu_clock;

osc_32 KHz is the raw slow clock from the crystal oscillator of slow clock generator 470;

32 KHz_slow is the slow clock developed in the slow clock generator 470 from the raw slow clock osc_32 KHz that clocks hardware circuitry until the slow sync clock is generated as described above;

mixed_clk is the slow clock 32 KHz_slow when the processor 410 is not clocked and the fast clock (cpu_clock) when the processor 410 is clocked;

osc_32 KHz_sync1, osc_32 KHz_sync2, and osc_32 KHz_sync3 are slow sync clocks developed from the 32 KHz_slow of which the osc_32 KHz_sync2 clock is the slow sync clock developed as described above to be synchronized to the E(raw) fast clock; and state represents the state machine states.

The initial state of the state machine 730 is an idle state (state 1110), and the slow clock (32 KHz_slow) is provided to the slow clock domain in the idle state 1110. The slow clock (32 KHz_slow) is the asynchronous 32 khz clock (osc_32 KHz) during the idle state and is the synchronized 32 khz clock (osc_32 KHz_sync2) when the cpu_clock is on.

In the wait states 1120 and 1130, the hardware asserts the "signal oscillator high frequency on" signal (osc_hf_on) that invokes the high frequency clock osc_hf(2.8 MHz), both shown in FIG. 12. The osc_hf(2.8 MHz) signal transitions the state machine 730 from the wait 0 state 1120 to the wait 1 state 1130 as shown in FIG. 11. The state 1140 is a wait state until the falling edge of the slow clock signal, particularly the osc_32 KHz_sync2 signal, occurs.

After the clock domains are synchronized in state 1150 of FIG. 11, the state machine 730 verifies that an interrupt is active. If an interrupt is active as determined in state 1150, the state machine 730 proceeds to state 1160 and turns on the cpu_clock shown in FIG. 12, switches the mixed_clk to the cpu_clock as shown in FIG. 12, and switches the 32 KHz_slow clock to the slow sync clock as described above (the osc_32 KHz_sync2 signal in FIG. 12). On the other hand, the state machine 730 goes to state 1170 to wait for a shut down request to turn off the clocks if no interrupt is determined to be active in state 1150.

State 1160 is maintained providing the fast clock to the fast clock domain and the synced slow clock to the slow clock domain until a shutdown request is generated by the firmware upon completion of the tasks invoked by the interrupt. The state machine 730 then goes to the wait-to-shut-down state 1170. In state 1170, the cpu_clock is turned off, but the osc_hf(2.8 MHz) is kept on and the slow sync clocks are maintained if required by fast clock domain portions of the hardware. The state machine 730 proceeds to state 1180 and turns off the osc_hf(2.8 MHz) clock if none of the hardware logic requires the high frequency clock to remain on (for example, no telemetry or high voltage capacitor charging is taking place). The state machine stays in state 1170 as long as the hardware requires the high frequency osc_hf(2.8 MHz) clock to remain on. Moreover, if an interrupt occurs, the state machine 730 goes back to state 1160 and the cpu_clock is again turned on and supplied to the processor 410 to carry out the firmware routine response to the specific interrupt. The state machine 730 returns to the idle state 1110 when shut down of the fast clock is completed in state 1180. Alternative embodiments of the implementation of the state machine 730 can be utilized within the spirit of the present invention.

The timing diagram illustrated in FIG. 12 tracks the operation of the state machine 730, as described above. Furthermore, Appendix A provides one method of invoking the state machine 730 using hardware descriptive language (HDL), as provided. Those skilled in the art, having the benefit of the present disclosure, can implement the state machine 730 described above by referring to the hardware descriptive language (HDL) provided in Appendix A. The switching of the clock frequencies and the synchronizing of the clock domains described by the present invention can be utilized in a variety of electrical circuits including medical devices, commercial devices, computing devices, and the like.

Thus, the processor 410 is clocked by the fast clock and performs its diagnostic and other data processing read/write functions in the fast clock domain in accordance with the firmware when certain states of the state machine 730 are satisfied. The slow clock is synchronized to the fast clock every time the fast clock is invoked.

When the processor 410 is clocked, the firmware dictates from time to time that the fast clock domain and the slow clock domain communicate over the data bus such that data bits are conveyed from the fast clock domain to the slow clock domain at the fast clock frequency, and the slow clock domain acknowledges the receipt of the data bits at the slow clock frequency. For example, the firmware of the processor 410 generates a data bit stream at the fast clock frequency of to the destination address on the address/data bus 425 and the data content to be written to a register at the address. The slow clock domain must be able to recognize that the bit stream is being sent to it, but the slow clock domain is clocked at such a relatively slow frequency relative to the data bit stream that the data bit stream could be completely or partly generated during a single slow clock cycle and not recognized.

Similarly, the slow clock domain must communicate with the fast clock domain when the fast clock is off or not applied to the fast clock domain.

Thus, it is necessary to provide hardware registers to hold data or status bits that can be queried by the slow clock domain at the slow clock frequency to determine if data has been communicated from the fast clock domain or queried by the fast clock domain at the fast clock frequency to determine if data has been communicated from the slow clock domain.

Figure 13A:
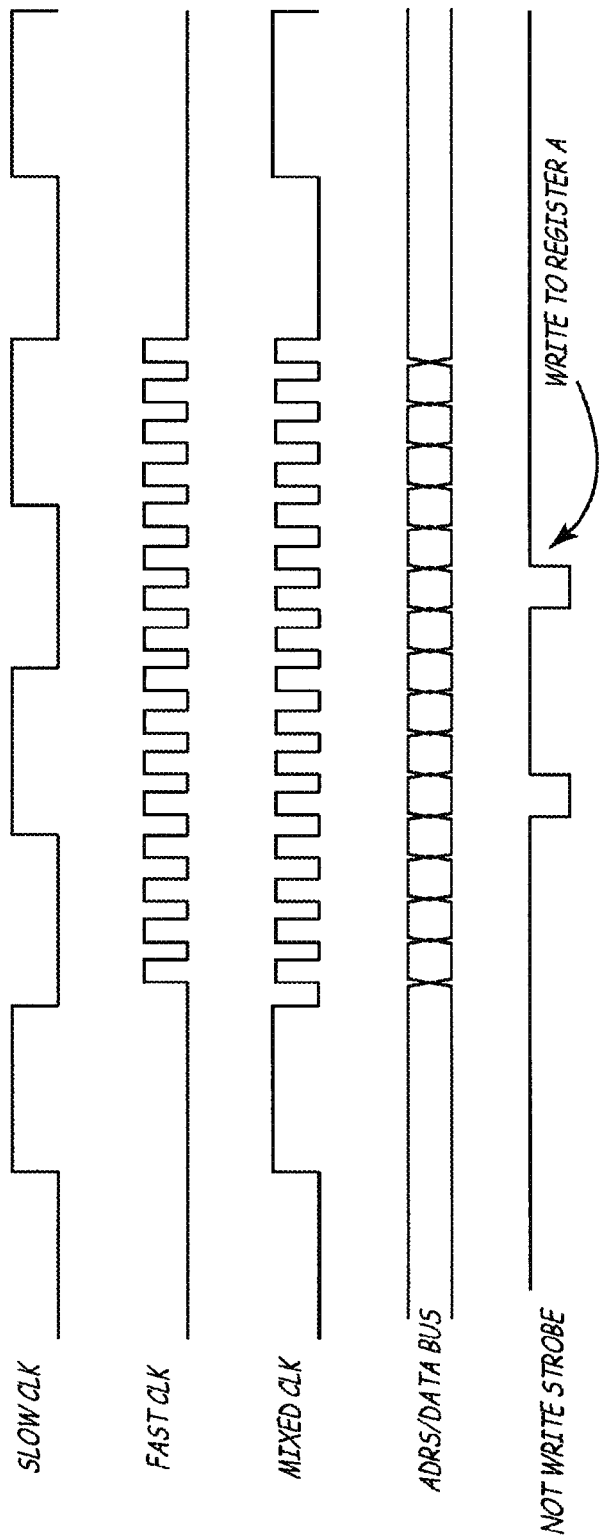
FIGS. 13a and 13b illustrate the function of writing data from a fast clock domain to a slow clock domain employing a mixed clock derived from the slow clock and the fast clock.
Figure 13B:
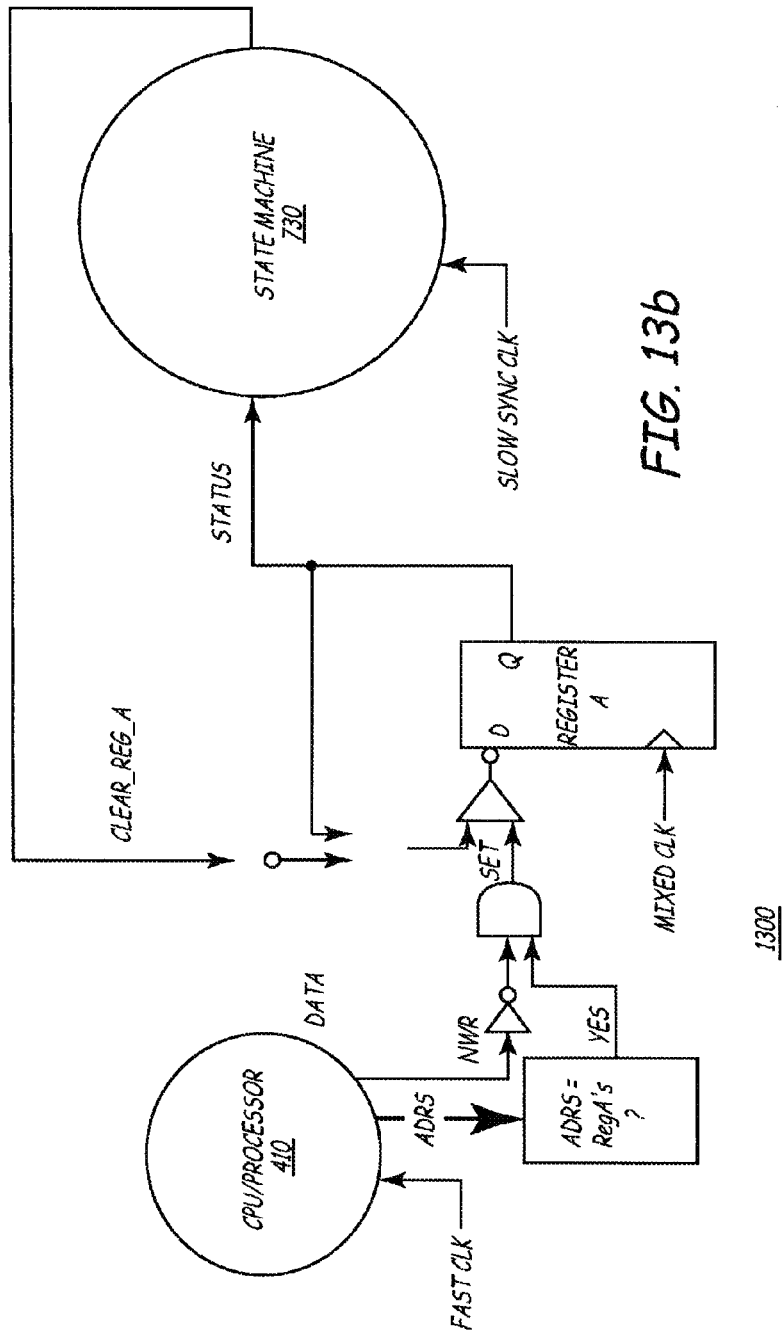

In accordance with one approach depicted in FIGS. 13A and 13B, and in reference again to FIGS. 7, 9, 11 and 12, a mixed clock (mixed_clk in FIG. 12) is generated at the same time that the slow sync clock is generated. The mixed clock comprises the slow clock until the fast clock is invoked or turned on and the fast clock until the fast clock is no longer invoked or turned off. The mixed clock is used to clock the registers holding such data communicated between the fast clock domain and the slow clock domain.

In FIG. 7, the slow clock is applied to the A input 744 of a second multiplexer 742, and the fast clock signal is applied to the B input 744 of the multiplexer 742. A select signal on the line 748 from the state machine 730 is applied to select input 743 of the multiplexer 742 for selection between the slow clock and the fast clock. Switching the mixed clock from the slow clock to the fast clock is accomplished by the state machine 730 in state 1160 of FIG. 11 to coincide with an interrupt and the development of the slow sync clock. Switching the mixed clock back to the slow clock is accomplished in state machine 730 in state 1180 upon a shut down request that turns the fast clock off. The mixed clock is depicted in FIGS. 12 and 13A.

Similarly, in FIG. 9, the slow clock is applied to the A input 944 of a second multiplexer 942, and the fast clock signal is applied to the B input 944 of the multiplexer 042. A select signal on the line 948 from the state machine 730 is applied to select input 943 of the multiplexer 942 for selection between the slow clock and the fast clock. Switching the mixed clock from the slow clock to the fast clock is accomplished by the state machine 730 in state 1160 of FIG. 11 to coincide with an interrupt and the development of the slow sync clock. Switching the mixed clock back to the slow clock is accomplished in state machine 730 in state 1180 upon a shut down request that turns the fast clock off. The mixed clock is depicted in FIGS. 12 and 13A.

The mixed clock is distributed to particular hardware registers of the slow clock domain that must be written to by the processor 410 and also written to by hardware 1300 clocked by the slow sync clock as is shown in FIGS. 13a and 13b. The slow sync clock and the mixed clock shown in FIG. 13a are generated as described above. When the processor 410 is clocked by the cpu_clock, it generates data bytes at the fast clock frequency on the address/data bus, each data byte having a data bit content and a data address. Certain of the data addresses are to registers in hardware 1300 that are cleared by a clear bit generated at the slow clock frequency in the idle state 1110 or generated at the slow sync clock frequency in the synced clock state 1160 as described above. Thus, certain data bytes contain a firmware generated address that specifies a hardware register (designated register A simply for convenience) within hardware 1300 of the slow clock domain that is to be written to, e.g., by being set (write 1). It is necessary to complete the write operation by clocking the register A at its clock input while the set data bit is applied to the set input of the register A. It is subsequently necessary to clear the register (write 0) by applying a clear signal from the firmware at the low clock frequency to the clear input of the register A.

Although only one register A of hardware 1300 is depicted in FIG. 13b, it will be understood that it represents a set of registers simultaneously receiving and being written to by the data bits of a data byte transmitted on the address/data bus from the processor. Each data bit at the set input would be a "1" or "0", whereby the registers would be set (write 1) or not set (write 0), respectively.

For example, firmware may request that the hardware 1300 clocked by the slow clock measure and digitize an analog signal employing A/D Conversion. The firmware would set a data bit in register A requesting the conversion. After requesting the conversion, the firmware may choose to shut down (go to sleep mode) to conserve power. When the hardware has completed the conversion, it clears the data bit in register A and generates an interrupt to wake up the firmware. The firmware can now read the data bit in register A and see that the conversion was completed.

It is not possible to write to register A using the slow clock to clock the register A when the data bit is directed to its set input by the processor 410 at the fast clock rate. It is likely that the data bit would be no longer applied to the set input when the slow clock edge clocks register A to accept it. Therefore, it is necessary to develop and apply the mixed clock to the clock input of register A so that the data bit and the clock are contemporaneously applied so that the register state can be written to as a 1 or 0.

The function and nature of register A expressed in the hardware description language is:
at ever rising edge of the mixed clock:
  if (write_to_address_A_by_cpu)
    register_a=data_from_cpu (a 1 would be a set)
  else if (write_register_A_by_hardware)
    register_a=data_from_hardware (a 0 would be a clear)
  else
    register_a=register_a (retain the previous value)

A "write_to_address A is effected in the tracings of FIG. 13A when the address of the data transmitted on the address/data bus identifies register A and the Not Write Strobe is low (nwr=0). The Not Write Strobe is implied in the Set signal of FIG. 13B. The signals are:
Set=(nwr=0) AND (address=Register A's address) AND (data=1).
Clear=A signal from the slow clock hardware to clear the data/status bit. Status=1 if Set, 0 if Clear, or the previous Status if not Set or Clear.

Once the data byte registers are written to, the state (1 or 0) of each such register A is available to the hardware. The hardware 1300 performs an operation signified by the data byte in the parallel registers, and then clears each register A. The processor 410 periodically polls (reads) the contents of the registers, and the firmware is advanced when the processor 410 determines that the register contents are cleared. In the interim, the mixed clock continues to be applied to the clock inputs of each register A, and that is wasteful of battery energy.

Figure 14A:
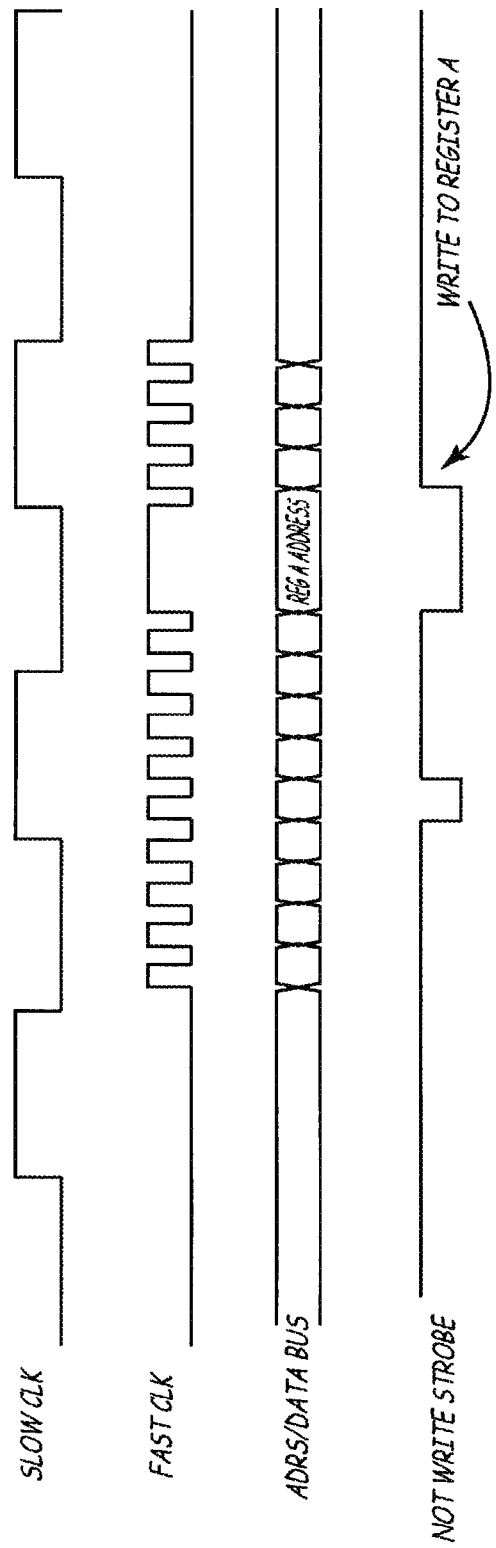
FIGS. 14a and 14b illustrate a system and method for writing data from a fast clock domain to a slow clock domain by pausing operation of the fast clock until the write is completed.
Figure 14B:
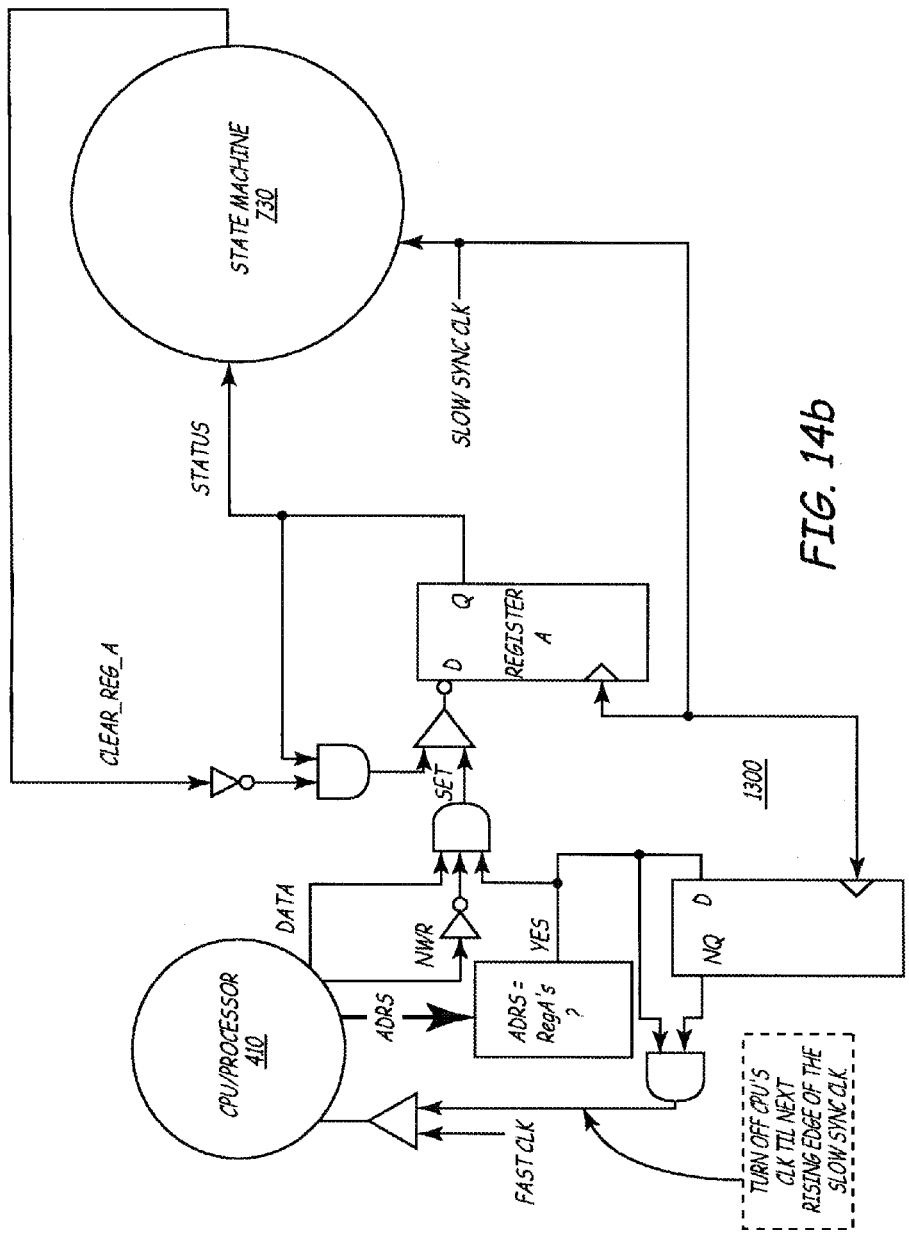
Figure 15:
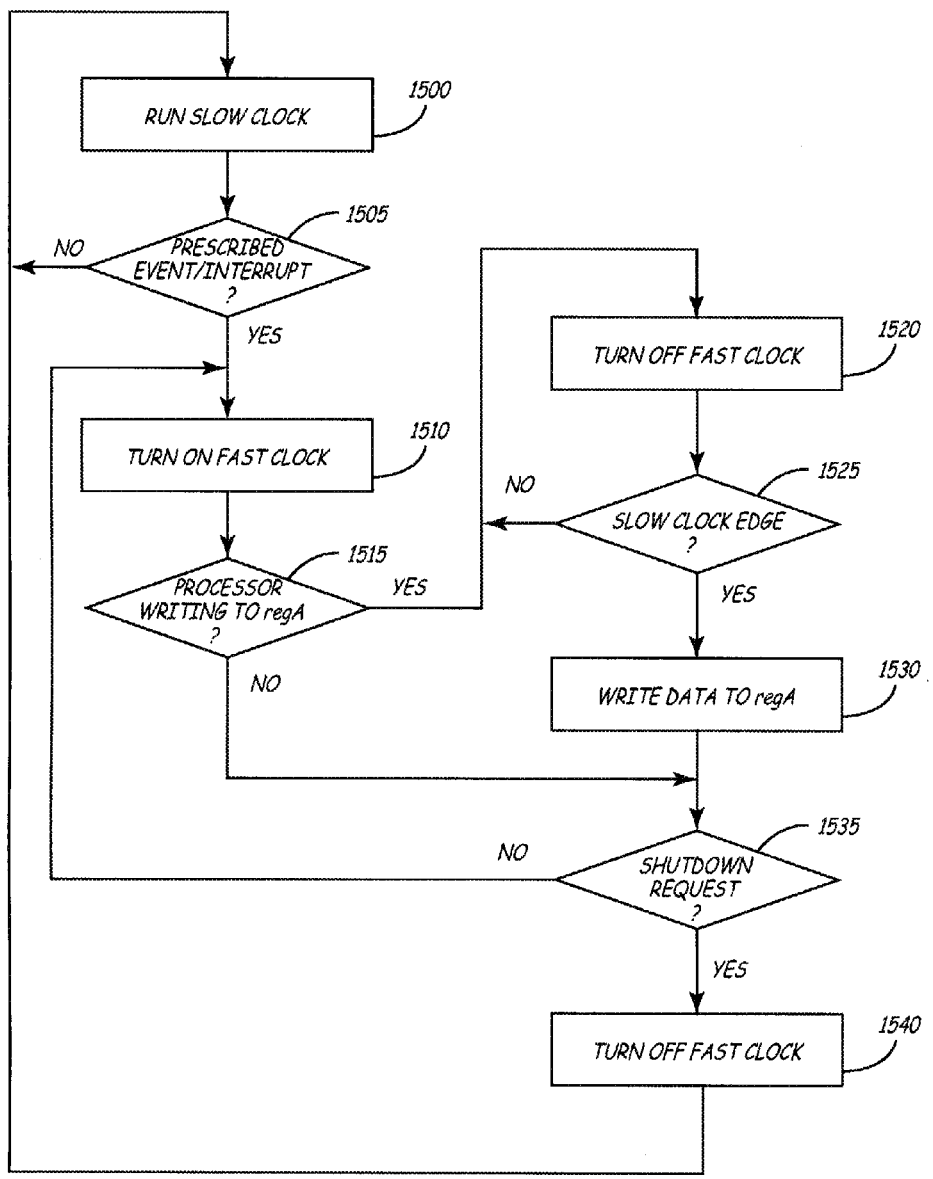
FIG. 15 is a flowchart illustrating the steps of operation of the system and method of FIGS. 14A and 14B.

A further improved system and method for reducing energy that eliminates the need to employ the mixed clock in this instance is illustrated in the timing diagram of FIG. 14a, the block diagram of FIG. 14b, and the flow chart of FIG. 15.

In accordance with the system depicted in FIGS. 14a and 14b, the slow clock is applied to the clock input of register A (as well as the parallel registers sharing the register A address) of hardware 1400. When write to register A is identified, the application of the fast clock to the processor 410 is interrupted or suspended until the next rising edge of the slow sync clock. The write signal (not write strobe in FIG. 14a) is extended long enough for the logic within the slow clock domain to clock the register A by suspending the application of the fast clock to the processor 410. Therefore, register A can now be clocked to be written to and later cleared at the slow clock frequency without applying the fast clock in the interim and thereby saving the power that the mixed clock would have expended.

FIG. 15 depicts operation of an IMD of the type performing monitoring of a physiologic state and/or therapy delivery under the control of a system comprising a processor that performs firmware routines and is clocked by a fast clock that is turned on when a prescribed event occurs to operate in a fast clock domain and hardware that performs certain device operations and is clocked by a slow clock that is always on, a method for writing data from the processor to the hardware.

In a normal operating mode, the slow clock is run in step 1500 as described above providing the slow clock to the slow clock domain and either turning off the fast clock or not applying the fast clock to some or all of the fast clock domain. A prescribed event, e.g., one of the above-described interrupts or requests, occurs in step 1505 requiring operation of the processor 410, and the fast clock 480 is applied to the fast clock domain to enable operation of the processor 410 in step 1510.

The data addresses of data to be written to the hardware by the processor is monitored in step 1515 to determine if a bit is to be written to a register of the slow clock domain that must be cleared in synchrony with a transition of the slow clock. When such an address is detected in step 1515, the operation of the processor 410 is paused in step 1520 by directly or indirectly stopping application of the fast clock to the processor 410.

The data is written to the address, e.g., register A, in step 1530 upon a following slow clock transition, typically the next slow clock transition occurring in step 1525. The fast clock is then restated in step 1510, and data continues to either be read or written to other addresses until a shut down request is generated by hardware in step 1535, and fast clock is turned off in step 1540.

It will be understood that "register A" of the above description can represent more than one slow clock domain address, and that the process of FIGS. 14A/14B and 15 applies to all such addresses of the slow clock domain.

It will also be understood that the system and process of the present invention can be practiced to facilitate data transfers between fast and slow clock domains that both comprise hardware driven by differing clocks. Similarly, it will be understood that the system and process of the present invention can be practiced to facilitate data transfers between fast and slow clock domains that both comprise firmware executed by processors that may or may not have particular hardware associated with the processor of each domain.

The above detailed description contains exemplary embodiments in accordance with teachings of the present invention. It should be appreciated that other implementations and/or embodiments can be employed within the spirit of the present invention. The teachings of the present invention can be utilized for a variety of systems relating to data acquisition, data storage, or presentation of data.

The particular embodiments disclosed above are exemplary only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. In an implantable medical device of the type performing monitoring of a physiologic state and/or therapy delivery under the control of a system comprising a processor that is clocked by a fast clock invoked when a prescribed event occurs and hardware that performs certain device operations and is clocked by a slow clock that is always on, a method for writing data from the processor to the hardware comprising:

providing the slow clock;
   detecting a prescribed event requiring operation of the processor;
   turning on the fast clock to enable operation of the processor;
   determining if a bit is to be written from the processor to a register of the hardware;
   pausing the fast clock to the processor until a next rising edge associated with the slow clock when a bit is to be written to the hardware register;
   writing the bit to the register of the hardware upon a slow clock transition while the fast clock to the processor is paused; and
   starting the fast clock at the next rising edge associated with the slow clock to resume operation of the processor.

2. The method of claim 1, further comprising the step of turning off the fast clock upon a shut down request.

* * * * *